US008191552B2

(12) United States Patent
Przekwas et al.

(10) Patent No.: US 8,191,552 B2
(45) Date of Patent: Jun. 5, 2012

(54) NEGATIVE PRESSURE, BI-DIRECTIONAL NASAL AEROSOL DELIVERY

(75) Inventors: Andrzej Przekwas, Huntsville, AL (US); Vincent Harrand, Huntsville, AL (US); Mark Papania, Lilburn, GA (US)

(73) Assignees: CFD Research Corporation, Huntsville, AL (US); Centers For Disease Control and Prevention, Atlanta, GA (US)

( * ) Notice: Subject to any disclaimer, the term of this patent is extended or adjusted under 35 U.S.C. 154(b) by 405 days.

(21) Appl. No.: 12/618,387

(22) Filed: Nov. 13, 2009

(65) Prior Publication Data

US 2010/0122697 A1 May 20, 2010

Related U.S. Application Data

(60) Provisional application No. 61/115,058, filed on Nov. 15, 2008.

(51) Int. Cl.
*A61M 11/00* (2006.01)

(52) U.S. Cl. ............................ 128/207.18; 128/203.22

(58) Field of Classification Search ............ 128/200.14, 128/200.21, 200.22, 203.12–203.18, 203.22, 128/206.11, 207.18
See application file for complete search history.

(56) References Cited

U.S. PATENT DOCUMENTS

| | | | | |
|---|---|---|---|---|
| 5,899,202 | A * | 5/1999 | Ohki et al. | 128/203.22 |
| 7,383,839 | B2 | 6/2008 | Porat et al. | |
| 7,481,218 | B2 * | 1/2009 | Djupesland | 128/206.11 |
| 2005/0072430 | A1 | 4/2005 | Djupesland | |
| 2006/0174886 | A1 * | 8/2006 | Curti et al. | 128/206.11 |
| 2007/0181133 | A1 | 8/2007 | Boehm et al. | |

FOREIGN PATENT DOCUMENTS

EP 1977778 A1 10/2008

* cited by examiner

*Primary Examiner* — Steven Douglas
(74) *Attorney, Agent, or Firm* — Maschoff Gilmore & Israelsen

(57) ABSTRACT

A method and apparatus for nasal drug delivery comprises a first tube in fluid communication with a means for generating a negative pressure and a second tube in fluid communication with an aerosol. The first tube is contacted with one nostril, the said second tube is contacted with the other nostril, and a negative pressure is applied to the first tube, producing a negative pressure within a nasal cavity and causing the aerosol to be drawn into the nasal passages and to deposit on an internal nasal surface.

25 Claims, 4 Drawing Sheets

PRIOR ART

Blowing causes Soft Palette to Close
High Pressure Injector System (Patient Blowing)

PRIOR ART

FIG. 4

Aerodynamic
Flow Focusing

Nebulize

NEGATIVE PRESSURE, BI-DIRECTIONAL NASAL AEROSOL DELIVERY

CROSS-REFERENCE TO RELATED APPLICATIONS

This application claims priority under 35 U.S.C. 119(e) to Provisional Patent Application Ser. No. 61/115,058, filed 15 Nov. 2008.

STATEMENT REGARDING FEDERALLY SPONSORED RESEARCH OR DEVELOPMENT

The U.S. Government has certain rights in this invention according to Contract 200-2007-M-22871 awarded by the Centers for Disease Control

BACKGROUND OF THE INVENTION

1. Field of the Invention

The invention related generally to nasal drug delivery. More specifically, the invention is a device and method for direct drug delivery primarily to nasal surfaces while minimizing drug delivery to the lungs and trachea.

2. Description of Related Art

Known nasal delivery systems use one of three methods: Natural Inspiration, Pressurized Delivery, and Bidirectional Delivery. Natural Inspiration delivers aerosol through a face mask and the subject inhales the aerosol. Pressurized Delivery sprays an aerosol into a nostril, or nasal nare, using positive pressure. Bidirectional Delivery requires the subject to blow into a nasal injector device, which causes the soft palette to close. Positive pressure produced by the subject blowing into the device injects aerosol into one nostril and into the nasal cavity. The use of a subject's breath to generate positive pressure, however, prevents reuse of the device by other subjects because of possible cross-contamination.

The known nasal aerosol delivery systems suffer from a number of limitations including the deposition of aerosol in the external nares, limited aerosol delivery beyond the nasal valve and onto internal nasal surfaces, and aerosol flow recirculation causing backflow into the nasal cavity, swallowing, and/or inhalation of aerosol. These limitations lead to inconsistencies in the effective dose of aerosol delivered using these methods.

BRIEF SUMMARY OF THE INVENTION

The present invention provides for a method and system for intranasal delivery of aerosols that overcomes the limitations of the known aerosol delivery systems and may be used to deliver aerosols comprising drugs including anesthetics, vaccines, metabolites, insulin, and odorants. The invention is particularly useful for targeting aerosol delivery beyond the nasal valve to the mucosal surfaces, which are lined by a single cell-thick columnar epithelium, and where inhalation or swallowing of drug is not desired. The invention is also particularly well suited for intranasal vaccine and antiviral drug delivery, as well as drug delivery to the central nervous system via olfactory neurons. The system can be fully automated and adapted for use in clinics, schools, and other non-clinical settings.

BRIEF DESCRIPTION OF THE DRAWINGS

Figure 4:
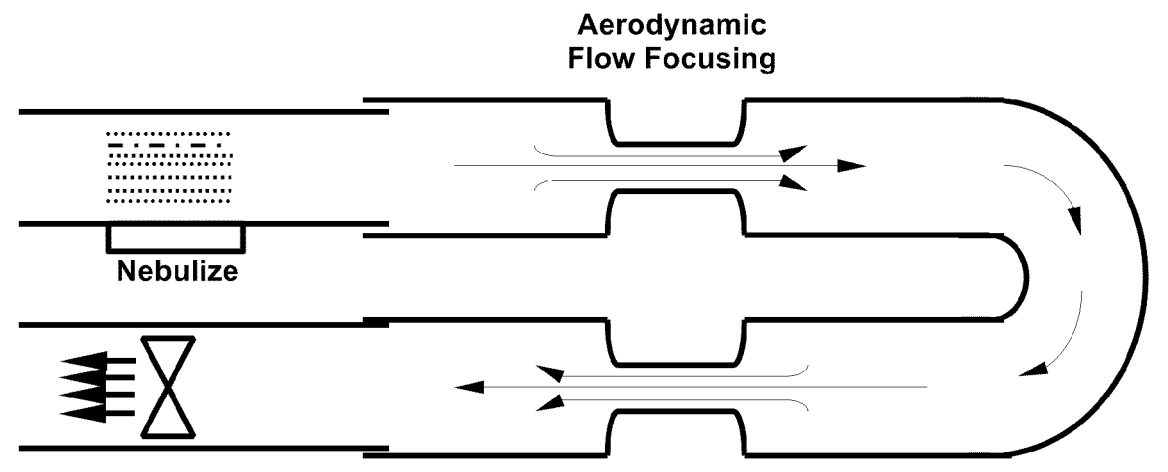

FIG. 4 is diagram representing intranasal aerodynamic flow generated by the present invention.

DETAILED DESCRIPTION OF THE INVENTION

As used herein, the term "internal nasal surfaces" is meant to include nasal epithelium, nasal associated lymphatic tissue, and olfactory tissues.

As used herein, positive and negative pressure refers to pressures that are greater than and less than ambient atmospheric pressure, respectively.

As used herein, "aerosol" refers to solid particulates and/or liquid droplets, including sprays, that are suspended in air or another gas.

"Bidirectional flow" as used herein refers to aerodynamic flow into one nostril of the nose simultaneously with aerodynamic flow out through the other nostril of the nose.

Figure 1:
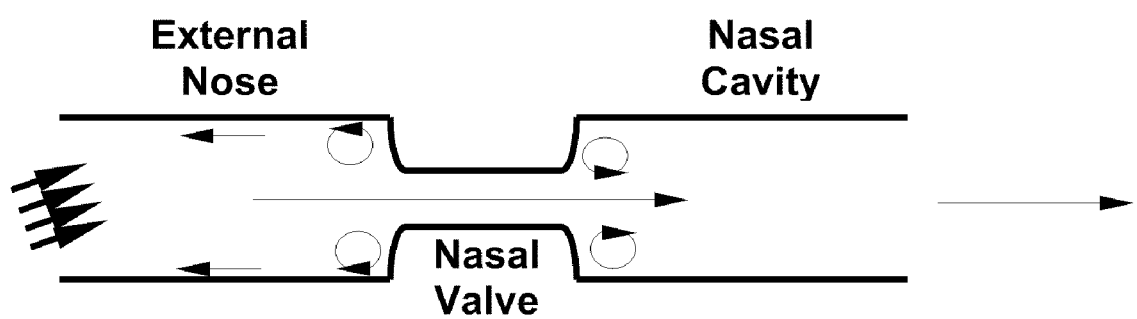
FIG. 1 is a diagram representing intranasal aerodynamic flow generated by a positive pressure nasal delivery apparatus according to the prior art.
Figure 2:
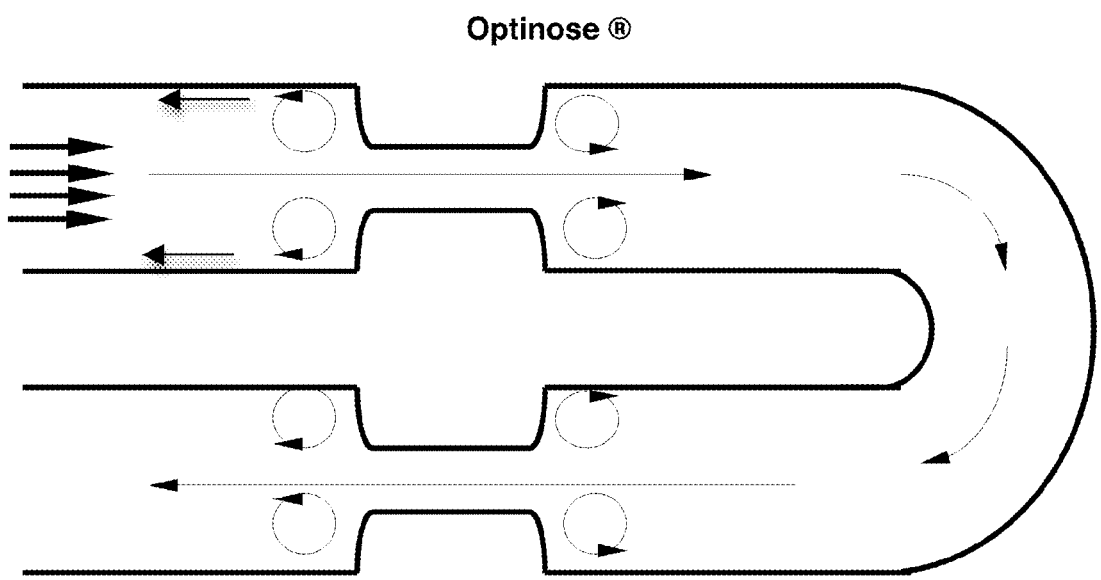
FIG. 2 is a diagram representing intranasal aerodynamic flow generated when the patient's mouth is used to provide positive pressure for a nasal delivery apparatus according to the prior art.

The use of conventional pressurized drug injection devices suffers from the disadvantage that drug deposits on the nasal valve, causing drug loss and variability in drug dose (FIG. 1 and FIG. 2). The inventors have found that, surprisingly, negative pressure, bidirectional nasal administration of an aerosol according to the present invention leads to natural aerodynamic flow focusing in the inlet nostril nasal valve, longer residence times for aerosols in the nasal cavity, higher aerosol deposition rates, and reduced aerosol deposition on the inlet nasal valve when compared to existing nasal aerosol delivery systems.

Figure 3:
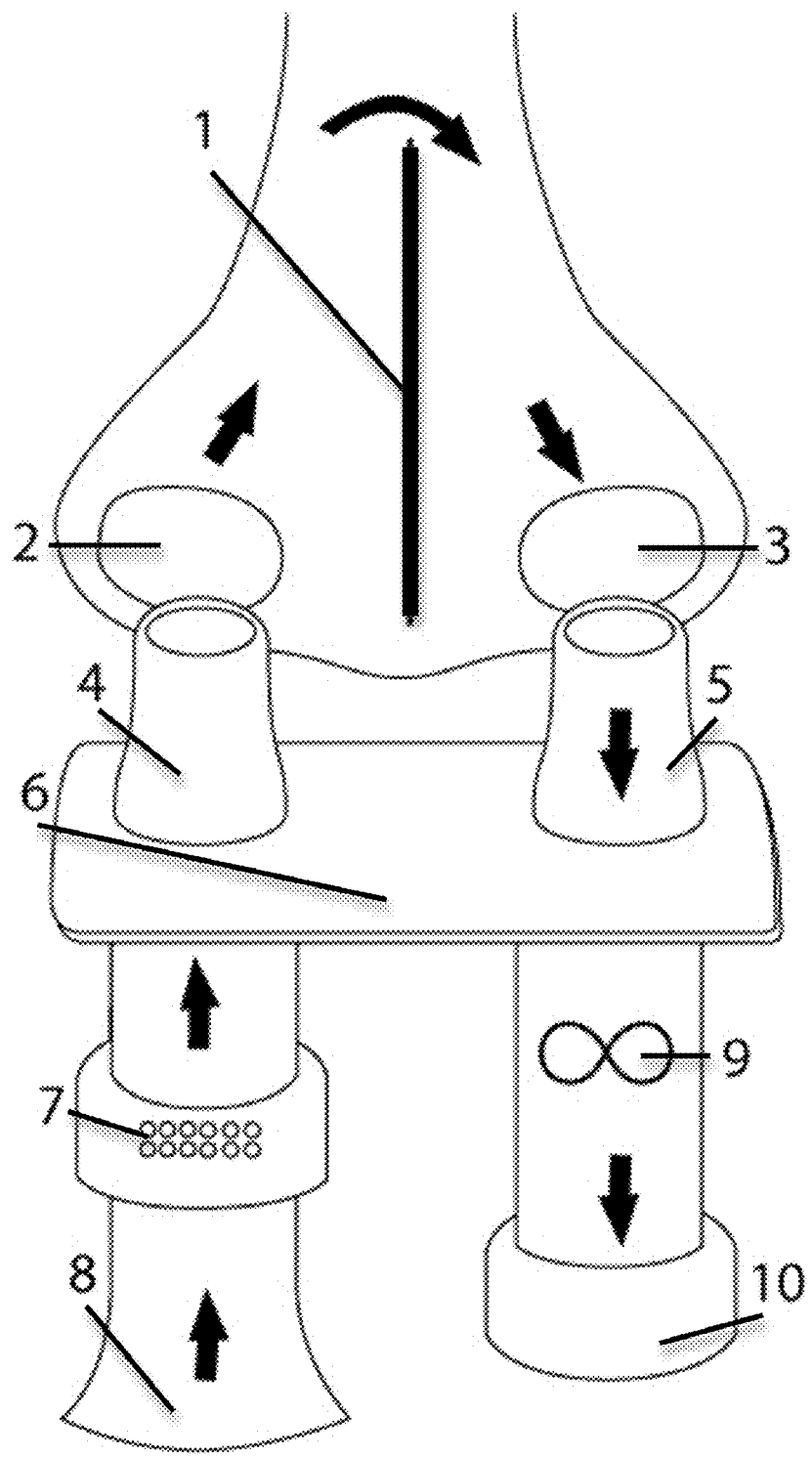
FIG. 3 is a schematic of one embodiment of the present invention.

An exemplary embodiment of a negative pressure, bidirectional nasal aerosol delivery apparatus is shown in FIG. 3. The apparatus comprises a negative pressure (suction), outlet duct 5 and a delivery inlet duct 4, optionally held by a spacer plate 6 that may be adjustable to control the spacing between the ducts (conduits). Outlet duct 5 is configured to attach to an exit nasal nare 3 (exit nostril) in such a way as to form a seal sufficient for pulling air out of the nose. Inlet duct 4 is configured to attach to an inlet nasal nare 2 (inlet nostril) in such a way as to form a seal sufficient for delivering an aerosolized agent. The aerosolized agent enters the inlet nostril 2, passes through the inlet concha to the back side of the nose, turns around the nasal septum 1, and is pulled through the other (outlet) concha, though the exit nasal nare 3 and into the suction outlet duct 5. A bi-directional flow from the inlet nostril 2 to the exit nostril 3 (indicated by large arrows) is created by means for producing a negative pressure in fluid communication with suction outlet duct 5. The means for producing a negative pressure may be, for example, a fan, an aspirator, a blower, an air pump, or a vacuum pump. The aerosol containing an agent comprising, for example, a vaccine or other drug, is released from a source of aerosol 7 connected to the delivery inlet duct 4, which is inserted into the inlet nostril 2. In contrast to existing systems, the aerosol spray is not pressure injected into a nostril, but is inspired with the inlet air.

In one embodiment, a subject's oral exhalation may be used to generate a negative pressure required for drawing air out of the exit nostril 3. Such an embodiment would ensure that the soft palate is closed during aerosol delivery and prevent pulmonary deposition. The apparatus may simultaneously use the subject's breath to provide energy for aerosolizing a powder or liquid and to generate a negative pressure. For example, the means for producing a negative pressure may comprise a tube configured to allow the subject to blow into a tube that has a narrow distal tip located in the distal end of the outlet duct to entrain collateral air and generate flow. Alternatively, a breath-driven fan or turbine may be located in a tube into which the subject blows. The breath-driven fan is mechanically coupled to a second fan, which generates a negative pressure. As another alternative, two parallel cylinders may be configured to contain mechanically coupled, pistons such that blowing into the first cylinder creates a positive pressure in the first piston. As the pressurized piston moves, it causes the second piston to generate a negative pressure in the second cylinder.

Depending on the level of sub-atmospheric pressure produced in the nose the oropharyngeal vellum, also known as soft palate, will move up and will partially or completely block aerosol delivery beyond the nasal cavity. Even if the soft palate is open, lowest flow resistance and the limited availability of air in the lung creates bi-directional flow from the inlet nostril to the exit nostril.

The bi-directional aerosol flow in the nasal cavity, and the 180° flow turn at the nasal posterior, create large centrifugal forces on aerosol particles or droplets and lead to aerosol deposition on nasal associated lymphatic tissue surfaces. Negative pressure also reduces nasal volume and increases the surface to volume ratio, further improving particle deposition efficiency. The suction conditions can be adjusted for specific nasal anatomy, nasal size, subject age, and nasal conditions.

The aerosol to be delivered is released from a nebulizer, humidifier, atomizer, or other aerosol producing means, connected to the delivery inlet duct, which is inserted into the inlet nostril. The aerosol may be delivered in an oscillatory fashion such that the velocity of the aerosol passing from the inlet nostril to the exit nostril is varied over time. Oscillatory delivery may be achieved by varying the negative pressure applied to the exit nostril, controlling a valve in the tube leading into the inlet and/or the exit nostril, and/or other means for controlling the resistance to aerodynamic flow within the nasal passages.

The aerosol delivery system may include an aerosol sensor that detects and quantifies the amount of aerosol that passes through the patient's nasal passages without being deposited. The information provided by the aerosol sensor may be used to control the operation of the system in a manual or automated fashion. For example, the negative pressure generated by a fan or pump may be controlled to reduce the negative pressure applied to the exit nostril if too much aerosol passes through the patient's nasal passages without depositing on an internal nasal surface. Another example of controlling the operation of the system is to control a valve between the inlet nostril and the aerosol generator to reduce the flow of aerosol through the nasal passages while reducing the pressure within the nasal passages, thereby causing a change in the contours within the nasal passages. Such a system may further comprise a pressure sensor located within the nasal passages of the patient as a safeguard to prevent reducing the pressure within the nasal cavity beyond a predetermined value and/or a predetermined rate of pressure change within the nasal cavity.

The nasal delivery system may include a filter for capturing aerosol exiting from the exit nostril to prevent the aerosol from contaminating the air after passing through the patient. Such aerosol, in addition to containing drug, may also contain pathogens or other biohazards originating within the patient. The filter is preferably a disposable filter placed between a disposable tube placed in the exit nostril and the fan, pump, or other means for producing a negative pressure.

What is claimed is:

1. A method for nasal delivery of an aerosol to a subject comprising the steps of:
    contacting a first conduit with a first of two nasal nares, said first conduit being in fluid communication with a means for generating a negative pressure;
    contacting a second conduit with a second of two nasal nares, said second conduit being in fluid communication with a source of aerosol; and
    applying a negative pressure to the first conduit, thereby producing a negative pressure within a nasal cavity connecting the two nasal nares and causing the aerosol to be drawn into the first nasal nare and causing at least a portion of the aerosol to deposit on an internal nasal surface.

2. The method of claim 1, wherein the means for generating a negative pressure is selected from the group consisting of a vacuum pump, an air pump, a fan, a blower, and an aspirator.

3. The method of claim 1, wherein the source of aerosol is selected from the group consisting of a nebulizer, an atomizer, and a humidifier.

4. The method of claim 1, wherein the means for generating a negative pressure is regulated to control the negative pressure generated.

5. The method of claim 4, wherein the negative pressure is controlled to open or close an oropharyngeal vellum.

6. The method of claim 1, further comprising the step of placing an aperture into the second nasal nare.

7. The method of claim 6, wherein the aperture is configured to control the trajectory of aerosolized drug drawn into the second nasal nare.

8. The method of claim 6, wherein the aperture is configured to control a pressure gradient between the nasal cavity and a lumen of the second conduit.

9. The method of claim 1, wherein the first and/or second conduits are replaceable and disposable.

10. The method of claim 1, wherein the source of aerosol is a device activated by aerodynamic flow induced by the means for generating a negative pressure.

11. The method of claim 10, wherein the duration of applying a negative pressure to the first conduit is used to control the dose of aerosol delivered.

12. The method of claim 1, wherein the negative pressure applied to the first nasal nare is changed during the step of applying a negative pressure or a resistance to aerodynamic flow between the aerosol source and the first nasal nare is changed during the step of applying a negative pressure.

13. The method of claim 1, wherein the aerosol comprises a drug.

14. The method of claim 1, wherein said means for producing a negative pressure is powered by the subject's breath.

15. An apparatus for delivering an aerosol to an internal nasal surface of a human or animal subject comprising:
    means for producing a negative pressure in fluid communication with the distal end of a first conduit, said first conduit having a proximal end configured to form a seal with a first nasal nare of the subject; and
    an aerosol source in fluid communication with the distal end of a second conduit, said second conduit having a proximal end configured to form a seal with a second nasal nare of the subject.

16. The apparatus of claim 15, wherein:
when the first and second conduits are configured such that, a negative pressure is produced within a nasal cavity of the subject when said means for producing a negative pressure is active, and
said negative pressure causes aerosol to be drawn into said second nostril from said aerosol source and at least a portion of said aerosol to be deposited on an internal nasal surface.

17. The apparatus of claim 15, further comprising an aerosol sensor configured to detect aerosol, and wherein said aerosol sensor is located between the first nasal nare and the means for producing a negative pressure.

18. The apparatus of claim 17, further comprising a control unit configured to control the negative pressure produced by the means for producing a negative pressure in response to a signal transmitted by the aerosol sensor.

19. The apparatus of claim 15, further comprising an aerosol filter configured to capture aerosol that is not deposited on an internal nasal surface, once the aerosol has exited the first nostril.

20. The apparatus of claim 15, wherein the means for producing a negative pressure is selected form the group consisting of a fan, an air pump, a vacuum pump, a blower, and an aspirator.

21. The apparatus of claim 15, wherein the source of aerosol is selected from the group consisting of a nebulizer, an atomizer, and a humidifier.

22. The apparatus of claim 15, wherein the first and second conduits are replaceable and disposable.

23. The apparatus of claim 15, and further comprising a valve configured to control the flow of aerosol into the second nasal nare.

24. The apparatus of claim 23, wherein the valve is located between the distal to the source of aerosol, between the source of aerosol and the second nasal nare, or between the source of negative pressure and the first nasal nare.

25. The apparatus of claim 15, wherein said means for producing a negative pressure is powered by the subject's breath.

* * * * *